United States Patent [19]

Parg et al.

[11] Patent Number: 4,537,621
[45] Date of Patent: Aug. 27, 1985

[54] HERBICIDAL DIPHENYL ETHERS AND THEIR USE FOR CONTROLLING UNDESIRABLE PLANT GROWTH

[75] Inventors: Adolf Parg, Bad Durkheim; Hans Ziegler, Mutterstadt; Bruno Wuerzer, Otterstadt, all of Fed. Rep. of Germany

[73] Assignee: BASF Aktiengesellschaft, Fed. Rep. of Germany

[21] Appl. No.: 481,100

[22] Filed: Mar. 31, 1983

[30] Foreign Application Priority Data

Apr. 1, 1982 [DE] Fed. Rep. of Germany ....... 3212165

[51] Int. Cl.³ ................ A61N 9/12; C07C 145/00
[52] U.S. Cl. ............................................ 71/103; 71/88;
71/92; 71/94; 71/95; 71/98; 260/239 A;
260/456 NS; 260/543 H; 544/159; 544/160;
544/383; 546/229; 546/230; 546/231; 548/542;
560/9; 560/12; 560/13; 560/17; 560/21;
562/430; 562/431; 564/102; 564/162; 564/341
[58] Field of Search ............ 260/543 H, 239 A, 465 F,
260/465 E, 465 D, 456 NS; 568/23, 38, 39, 44,
45, 51; 560/9, 21, 17, 12, 13, ; 562/431, 430;
564/162, 341, 102; 546/230, 229, 231; 548/542;
71/98, 103, 92, 94, 95, 88; 544/159, 160, 383

[56] References Cited

U.S. PATENT DOCUMENTS 3,784,635  1/1974  Theissen ..................... 260/465 D
4,213,775  7/1980  Nagai et al. .................... 71/103
4,370,340  1/1983  Ueda et al. ..................... 424/274

FOREIGN PATENT DOCUMENTS 21320  7/1979  Japan .

OTHER PUBLICATIONS

Yoshimoto et al., C.A., 91–192987a, (1979).
Yoshimoto et al., C.A. 93–7835e, (1980).

*Primary Examiner*—Nicky Chan
*Attorney, Agent, or Firm*—Keil & Weinkauf

[57] ABSTRACT

Diphenyl ethers of the formula

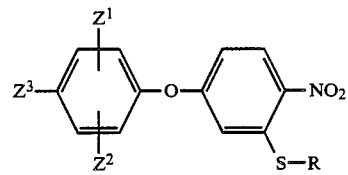

where $Z^1$, $Z^2$, and $Z^3$ and R have the meanings given in the description, are used for controlling undesirable plant growth.

10 Claims, No Drawings

HERBICIDAL DIPHENYL ETHERS AND THEIR USE FOR CONTROLLING UNDESIRABLE PLANT GROWTH

The present invention relates to diphenyl ethers, herbicides containing these compounds as active ingredients, and their use for controlling undesirable plant growth.

Active ingredients from the class of diphenyl ethers possessing a thio radical ortho to the nitro group have been disclosed in the Literature (Japanese Preliminary Published Application No. 77/21,320 and German Laid-Open Application DOS No. 2,833,021).

We have found that diphenyl ethers of the formula

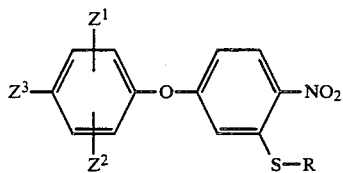

(I)

where $Z^1$ and $Z^2$ independently of one another are each hydrogen, halogen, nitro, cyano, carboxyl, $C_1$–$C_4$-alkyl, $C_1$–$C_4$-haloalkyl or $C_1$–$C_4$-alkoxy, $Z^3$ is halogen, nitro, cyano, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylmercapto, $C_1$–$C_4$-haloalkylmercapto, $C_1$–$C_4$-alkylsulfinyl, $C_1$–$C_4$-haloalkylsulfinyl, $C_1$–$C_4$-alkylsulfonyl or $C_1$–$C_4$-haloalkylsulfonyl, and R is hydrogen, halogen or —X—$R^1$, where X is oxygen or sulfur and $R^1$ is hydrogen, $C_1$–$C_{20}$-alkyl, $C_1$–$C_{20}$-alkoxyalkyl, $C_1$–$C_{20}$-alkylthioalkyl, $C_2$–$C_{20}$-alkylaminoalkyl, $C_3$–$C_{20}$-dialkylaminoalkyl, $C_1$–$C_{20}$-haloalkyl, an unsubstituted or halogen-substituted araliphatic radical of 7 to 20 carbon atoms, $C_2$–$C_8$-alkenyl, $C_2$–$C_8$-haloalkenyl or $C_2$–$C_8$-alkynyl of not more than 8 carbon atoms, carboxyalkyl, alkoxycarbonylalkyl or carbamylalkyl of not more than 6 carbon atoms, cycloalkyl of 3 to 20 carbon atoms or unsubstituted or substituted phenyl, or R is —$NR^2R^3$, where $R^2$ and $R^3$ are identical or different and have the meanings stated for $R^1$, or if $R^3$ is hydrogen or $C_1$–$C_4$-alkyl, $R^2$ is hydroxyl or $C_1$–$C_{20}$-alkoxy, or is $C_1$–$C_{20}$-alkoxy which is substituted by $C_1$–$C_6$-alkoxy, $C_1$–$C_6$-alkylthio, $C_1$–$C_6$-alkylamino, $C_2$–$C_6$-dialkylamino, halogen, carboxyalkyl, alkoxycarbonyl or phenyl, or is unsubstituted or substituted phenoxy or unsubstituted, $C_1$–$C_{20}$-alkyl-substituted or phenyl-substituted amino, or $R^2$ and $R^3$ together form an alkylene chain of 4 or 5 carbon atoms which is unsubstituted or monosubstituted or polysubstituted by $C_1$–$C_4$-alkyl and can be interrupted by oxygen or nitrogen, possess total or selective herbicidal activity, depending on formulation and dosage rate.

In formula I, $Z^1$ and $Z^2$ independently of one another are each hydrogen, halogen, nitro, cyano, carboxyl, $C_1$–$C_4$-alkyl, $C_1$–$C_4$-haloalkyl or $C_1$–$C_4$-alkoxy, eg. fluorine, chlorine, bromine, iodine, methyl, ethyl, n-propyl, i-propyl, n-butyl, tert.-butyl, trifluoromethyl, difluoromethyl, fluoromethyl, trichloromethyl, dichloromethyl, chloromethyl, difluorochloromethyl, 1-chloroethyl, 2-chloroethyl, 1-fluoroethyl, 2-fluoroethyl, 2,2,2-trichloroethyl, 2,2,2-trifluoroethyl, 1,1,2,2-tetrafluoroethyl, 1,1,2-trifluoro-2-chloroethyl, 1,1,2,2,2-pentafluoroethyl, methoxy, ethoxy, n-propoxy, i-propoxy or tert.-butoxy, $Z^3$ is halogen, nitro, cyano, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylmercapto, $C_1$–$C_4$-haloalkylmercapto, $C_1$–$C_4$-alkylsulfinyl, $C_1$–$C_4$-haloalkylsulfinyl, $C_1$–$C_4$-alkylsulfonyl or $C_1$–$C_4$-haloalkylsulfonyl, eg. fluorine, chlorine, bromine, iodine, methyl, ethyl, n-propyl, i-propyl, n-butyl, tert.-butyl, trifluoromethyl, difluoromethyl, fluoromethyl, trichloromethyl, dichloromethyl, chloromethyl, difluorochloromethyl, 1-chloroethyl, 2-chloroethyl, 1-fluoroethyl, 2-fluoroethyl, 2,2,2-trichloroethyl, 2,2,2-trifluoroethyl, 1,1,2,2-tetrafluoroethyl, 1,1,2-trifluoro-2-chloroethyl, 1,1,2,2,2-pentafluoroethyl, methoxy, ethoxy, n-propoxy, i-propoxy, tert.-butoxy, trichloromethoxy, trifluoromethoxy, 1-chloroethoxy, 2-chloroethoxy, 1-fluoroethoxy, 2-fluoroethoxy, 2,2,2-trichloroethoxy, 2,2,2-trifluoroethoxy, 1,1,2,2-tetrafluoroethoxy, 1,1,2,2,2-pentafluoroethoxy, methylmercapto, ethylmercapto, trichloromethylmercapto, trifluoromethylmercapto, methylsulfinyl, ethylsulfinyl, methylsulfonyl, ethylsulfonyl or trifluoromethylsulfonyl, and R is hydrogen, halogen, eg. fluorine, chlorine or bromine, —$XR^1$ or —$NR^2R^3$.

In the radical —$XR^1$, $R^1$ is hydrogen or alkyl of 1 to 20, preferably 1 to 4, carbon atoms, eg. methyl, ethyl, n-propyl, prop-2-yl, n-butyl, tert.-butyl or one of the isomeric pentyl, hexyl or heptyl radicals, alkoxyalkyl of 2 to 20, in particular 2 to 6, carbon atoms, eg. methoxymethyl, ethoxymethyl, methoxyethyl, methoxypropyl, methoxybutyl or ethoxybutyl, alkylthioalkyl of 2 to 20, in particular 2 to 6, carbon atoms, eg. methylthiomethyl, ethylthiomethyl, methylthioethyl, methylthiopropyl, methylthiobutyl or ethylthiopropyl, alkylaminoalkyl of 2 to 20, in particular 2 to 6, carbon atoms, eg. methylaminomethyl, methylaminoethyl, ethylaminomethyl, ethylaminoethyl, methylaminopropyl or methylaminobutyl, dialkylaminoalkyl of 3 to 20, in particular 3 to 8, carbon atoms, eg. dimethylaminomethyl, dimethylaminoethyl, diethylaminoethyl, diethylaminopropyl or diethylaminobutyl, haloalkyl of 1 to 20, in particular 1 to 4, carbon atoms, eg. chloromethyl, trichloromethyl, 2-chloroethyl, 2-fluoroethyl, 3-chloropropyl or 4-chlorobutyl, an unsubstituted or halogen-substituted araliphatic radical of 7 to 20, in particular 7 to 9, carbon atoms, eg. benzyl, 4-chlorobenzyl, 2,4-dichlorobenzyl, phenylethyl or phenylpropyl, alkenyl, haloalkenyl or alkynyl, each of 2 to 8, in particular 2 to 4, carbon atoms, eg. ethenyl, propen-1-yl, propen-2-yl, chloroethenyl, ethynyl, propargyl or butynyl, or a carboxyalkyl radical of the formula —$(CHR^4)_n$—COOH, where $R^4$ is hydrogen, methyl, ethyl or propyl and n is 1, 2 or 3, or $R^1$ is an alkoxycarbonylalkyl radical of the formula —$(CHR^4)_n$COO$R^5$, where $R^4$ and n have the above meanings and $R^5$ is alkyl of 1 to 20, in particular 1 to 4, carbon atoms, eg. methyl, ethyl, propyl or butyl, or $R^1$ is a carbamylalkyl radical of the formula —$(CHR^4)_n$—CO—$NR^6R^7$, where $R^4$ and n have the above meanings and $R^6$ and $R^7$ are identical or different and are each hydrogen, $C_1$–$C_4$-alkyl, eg. methyl or ethyl, or phenyl which is unsubstituted or substituted by halogen, $C_1$–$C_4$-alkyl, $C_1$–$C_4$-haloalkyl, such as trifluoromethyl, or cyano, or $R^6$ and $R^7$ together form an alkylene chain of 4 to 6 carbon atoms, or $R^1$ is cycloalkyl of 3 to 20, in particular 3 to 6, carbon atoms, eg. cyclopropyl, cyclobutyl, cyclopentyl or cyclohexyl, or is phenyl which is unsubstituted or substituted by halogen, $C_1$–$C_4$-alkyl, eg. methyl or ethyl, $C_1$–$C_4$-haloalkyl, eg. trifluoromethyl, cyano or an alkoxycarbonylalkoxy radical of the formula —O—$(CHR^4)_n$—COO$R^5$, where $R^4$, $R^5$ and n have the above meanings, eg. 1-n-butoxycarbonylethoxy.

In the radical —NR²R³, R² and R³ are identical or different and have the meanings stated for R¹. Where R³ is hydrogen or $C_1$-$C_4$-alkyl, R² may furthermore be hydroxyl, alkoxy of 1 to 20, preferably 1 to 4, carbon atoms, eg. methoxy, ethoxy, propoxy or butoxy, or alkoxy of 1 to 20 carbon atoms which is substituted by $C_1$-$C_8$-alkoxy, $C_1$-$C_8$-alkylthio, $C_1$-$C_8$-alkylamino, $C_2$-$C_8$-dialkylamino, halogen, carboxyalkyl, alkoxycarbonyl or phenyl, eg. methoxymethoxy, methoxyethoxy, methylthiomethoxy, methylthioethoxy, methylaminoethoxy, dimethylaminoethoxy, chloroethoxy, fluoroethoxy, carbonylmethoxy, methoxycarbonylmethoxy, 2-methoxycarbonylethoxy, benzyloxy or phenylethoxy, or may be unsubstituted, halogen-substituted or $C_1$-$C_4$-alkyl-substituted phenoxy, eg. phenoxy, 4-chlorophenoxy, 2,4-dichlorophenoxy or 4-methylphenoxy, or may be amino which is unsubstituted or substituted by alkyl of 1 to 20, preferably 1 to 8, carbon atoms, or by phenyl which is unsubstituted or substituted by halogen, cyano, nitro, $C_1$-$C_4$-alkyl or $C_1$-$C_4$-haloalkyl, eg. methylamino, ethylamino, propylamino, butylamino, pentylamino, phenylamino, 4-chlorophenylamino, 2,4-dichlorophenylamino, 4-cyanophenylamino, 3-trifluoromethylphenylamino, 4-methylphenylamino or 4-nitrophenylamino. R² and R³ together may furthermore form an alkylene chain of 4 or 5 carbon atoms which is unsubstituted or monosubstituted or polysubstituted by $C_1$-$C_4$-alkyl and can be interrupted by oxygen or nitrogen; together with the nitrogen atom to which they are bonded, they then form, for example, one of the following radicals: azetidino, pyrrolidino, piperidino, morpholino, 2,6-dimethylmorpholino, piperazino, 2,6-dimethylpiperazino, N-methylpiperazino or N-ethylpiperazino, $Z^1$, $Z^2$ and $Z^3$ are preferably at the 2, 4 and 6 positions of the phenyl ring.

Preferred diphenyl ethers are compounds of the formula I where $Z^1$, $Z^2$ and $Z^3$ independently of one another are each hydrogen, halogen, $C_1$-$C_4$-haloalkyl or $C_1$-$C_4$-haloalkylmercapto, and R is —X—R¹, where X is oxygen or sulfur and R¹ is $C_1$-$C_8$-alkyl, $C_2$-$C_6$-alkoxyalkyl, $C_2$-$C_6$-alkylthioalkyl, $C_2$-$C_6$-carboxyalkyl or $C_3$-$C_6$-alkoxycarbonylalkyl. Further preferred compounds are those in which $Z^1$, $Z^2$ and $Z^3$ have the last-mentioned meanings and R is —NR²R³, where R² and R³ are identical or different and are each hydrogen, $C_1$-$C_{10}$-alkyl, $C_2$-$C_6$-alkoxy alkyl, $C_2$-$C_6$-alkylthioalkyl or unsubstituted or halogen-substituted phenyl, or where R³ is hydrogen or $C_1$-$C_4$-alkyl and R² is $C_1$-$C_{14}$-alkoxy or unsubstituted or $C_1$-$C_8$-alkyl-substituted amino. Particularly preferred diphenyl ethers are those of the formula I where $Z^1$ is hydrogen, $Z^2$ and $Z^3$ are each halogen or $C_1$-$C_4$-haloalkyl and R is —X—R¹, where X is oxygen and R¹ is $C_1$-$C_4$-alkyl.

Diphenyl ethers of the formula I where R is halogen are obtained by a process wherein an ether of the formula

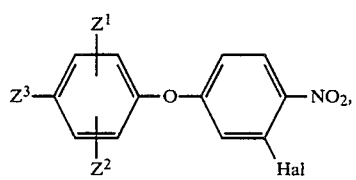

where $Z^1$, $Z^2$ and $Z^3$ have the above meanings and Hal is halogen, is reacted with not less than the stoichiometric amount of sodium disulfide, in the presence of an organic solvent at from 0° to 120° C., in particular from 20° to 80° C., to give the disulfide of the formula

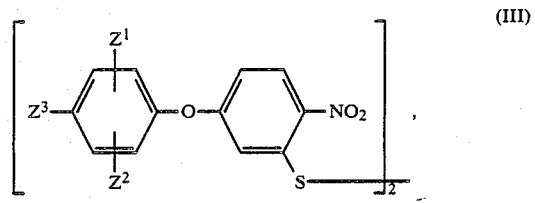

where $Z^1$, $Z^2$ and $Z^3$ have the above meanings, and this disulfide is then reacted with not less than the stoichiometric amount of elementary halogen in the presence of an inert organic solvent at from $-20°$ to $+120°$ C., in particular from 0° to 100° C. Both reactions can be carried out batchwise or continuously, under atmospheric or superatmospheric pressure.

Diphenyl ethers of the formula I where R is hydrogen, —XR¹ or —NR²R³ are obtained by a process wherein a sulfenyl halide of the formula

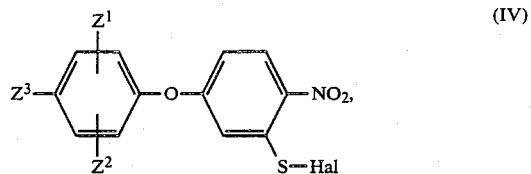

where $Z^1$, $Z^2$ and $Z^3$ have the above meanings and Hal is halogen, is reacted with not less than an equimolar amount of a compound of the formula

R—H (V), where R has the above meanings, in an inert organic solvent and in the presence or absence of an acid acceptor, at from $-20°$ to $+150°$ C., in particular from 0° to 120° C. The reaction can be carried out continuously or batchwise, under atmospheric or superatmospheric pressure.

The process for the preparation of the disulfides of the formula III can be represented by the following equation:

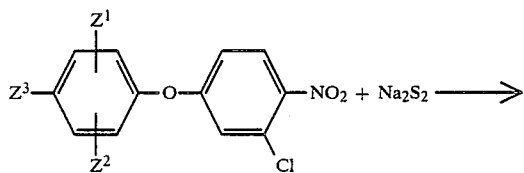

(II)

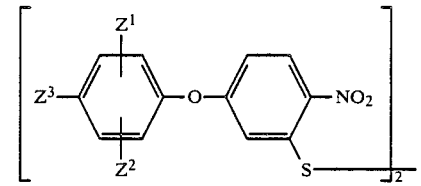

(III)

The starting materials are employed in about stoichiometric amounts, but it is preferable to use an excess of not more than 10%, based on II, of sodium disulfide. The process is advantageously carried out as follows: an equimolar amount of the halogen compound II is added to a suspension of sodium disulfide in an organic solvent, and the reaction is completed by stirring the mixture for from 0.5 to 48, preferably from 2 to 12, hours at from 0° to 80° C. The reaction mixture is filtered under suction or evaporated down, and the desired end product can be isolated by dissolving and reprecipitating, by recrystallization or by stirring with water.

The process for the preparation of the sulfenyl halides of the formula IV can be represented by the following equation:

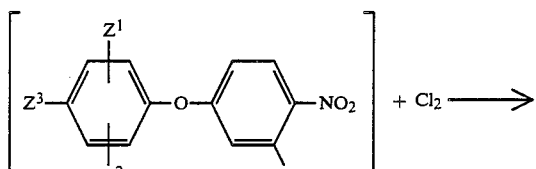

(III)

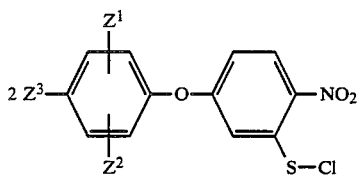

(IV)

The starting materials are employed in about stoichiometric amounts, but it is preferable to use an excess of not more than 30%, based on III, of halogen. The process is advantageously carried out as follows: not less than an equimolar amount of halogen is added to a suspension or solution of the disulfide in an inert organic solvent. The reaction is completed by stirring for from 0.5 to 48, preferably from 2 to 12, hours at from 0° to 100° C. The reaction mixture is evaporated down, and the desired end product can be isolated by dissolving and reprecipitating, by recrystallization or by chromatography.

The process for the preparation of the diphenyl ether of the formula I where R is hydrogen, —XR¹ or —NR²R³ can be represented, for example, by the following equation:

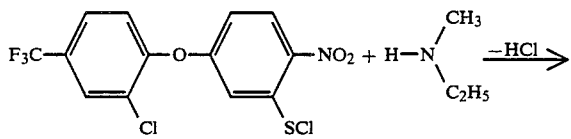

-continued

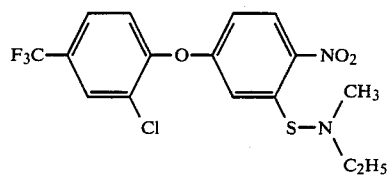

The starting materials are employed in about stoichiometric amounts, ie. from 0.9 to 1.1 moles of starting material V per mole of IV. To complete the reaction, an acid acceptor may, if required, be added, and, where starting material V is an amine, this compound may itself act as the acid acceptor. Furthermore, the hydrogen halide formed during the reaction can be removed by flushing with an inert gas, eg. nitrogen. Advantageously, the process is carried out as follows: a solution of the sulfenyl halide IV in an inert organic solvent, if appropriate together with an equimolar amount of an acid acceptor, is run into a solution of starting material V in an inert organic solvent, at from −20° to +150° C., preferably from 0° to +120° C.

To complete the reaction, stirring is continued for from 0.5 to 48, preferably from 2 to 12, hours at from 0° to 60° C. The reaction mixture is evaporated down, and the desired end product can be isolated by dissolving and reprecipitating, by recrystallization or by stirring with water, and, if required, can be purified by chromatography.

Both processes are carried out using organic solvents which are inert under the particular conditions. Examples of suitable solvents are halohydrocarbons, in particular chlorohydrocarbons, eg. tetrachloroethylene, 1,1,2,2- and 1,1,1,2-tetrachloroethane, dichloropropane, methylene chloride, dichlorobutane, chloroform, chloronaphthalene, dichloronaphthalene, carbon tetrachloride, 1,1,1- and 1,1,2-trichloroethane, trichloroethylene, pentachloroethane, o-, m- and p-difluorobenzene, 1,2-dichloroethane, 1,1-dichloroethane, 1,2-cis-dichloroethylene, chlorobenzene, fluorobenzene, bromobenzene, iodobenzene, o-, p- and m-dichlorobenzene, o-, p- and m-dibromobenzene, o-, m- and p-chlorotoluene and 1,2,4-trichlorobenzene, ethers, eg. ethyl propyl ether, methyl tert.-butyl ether, n-butyl ethyl ether, di-n-butyl ether, diisobutyl ether, diisoamyl ether, diisopropyl ether, anisole, phenetole, cyclohexyl methyl ether, diethyl ether, ethylene glycol dimethyl ether, tetrahydrofuran, dioxane, thioanisole and $\beta,\beta'$-dichlorodiethyl ether, nitrohydrocarbons, eg. nitromethane, nitroethane, nitrobenzene, o-, m- and p-chloronitrobenzene and o-nitrotoluene, nitriles, eg. acetonitrile, butyronitrile, isobutyronitrile, benzonitrile and m-chlorobenzonitrile, aliphatic and cycloaliphatic hydrocarbons, eg. heptane, pinane, nonane, o-, m- and p-cymene, gasoline fractions boiling within a range from 70° to 190° C., cyclohexane, methylcyclohexane, decalin, petroleum ether, hexane, naphtha, 2,2,4-trimethylpentane, 2,2,3-trimethylpentane, 2,3,3-trimethylpentane and octane, esters, eg. ethyl acetate, ethyl acetoacetate and isobutyl acetate, amides, eg. formamide, methylformamide and dimethylformamide, ketones, eg. acetone and methyl ethyl ketone, and mixtures of these solvents. Advantageously, the solvent is used in an amount of from 100 to 2,000, preferably from 200 to 700, % by weight, based on the starting materials.

Any conventional acid acceptor can be employed. Preferred acid acceptors include tertiary amines, alkaline earth metal compounds, ammonium compounds and alkali metal compounds as well as mixtures of these, but zinc compounds may also be used. Examples of suitable basic compounds are potassium hydroxide, sodium hydroxide, potassium carbonate, sodium carbonate, lithium hydroxide, lithium carbonate, sodium bicarbonate, potassium bicarbonate, calcium hydroxide, calcium oxide, barium oxide, magnesium hydroxide, magnesium oxide, barium hydroxide, calcium carbonate, magnesium carbonate, magnesium bicarbonate, magnesium acetate, zinc hydroxide, zinc oxide, zinc carbonate, zinc bicarbonate, zinc acetate, sodium formate, sodium acetate, trimethylamine, triethylamine, tripropylamine, triisopropylamine, tributylamine, triisobutylamine, tri-sec.-butylamine, tri-tert.-butylamine, tribenzylamine, tricyclohexylamine, triamylamine, diisopropylethylamine, trihexylamine, N,N-dimethylaniline, N,N-diethylaniline, N,N-dipropylaniline, N,N-dimethyltoluidine, N,N-diethyltoluidine, N,N-dipropyltoluidine, N,N-dimethyl-p-aminopyridine, N,N-diethyl-p-aminopyridine, N,N-dipropyl-p-aminopyridine, N-methylpyrrolidone, N-ethylpyrrolidone, N-methylpiperidine, N-ethylpiperidine, N-methylpyrrolidine, N-ethylpyrrolidine, N-methylimidazole, N-ethylimidazole, N-methylpyrrole, N-ethylpyrrole, N-methylmorpholine, N-ethylmorpholine, N-methylhexamethyleneimine, N-ethylhexamethyleneimine, pyridine, quinoline, α-picoline, β-picoline, γ-picoline, isoquinoline, pyrimidine, acridine, N,N,N',N'-tetramethylethylenediamine, N,N,N',N'-tetraethylethylenediamine, quinoxaline, quinazoline, N-propyldiisopropylamine, N,N'-dimethylcyclohexylamine, 2,6-lutidine, 2,4-lutidine, trifurylamine and triethylenediamine.

The starting compounds are prepared by a conventional method. Thus, the ethers of the formula II are obtained by the procedure described in German Laid-Open Application DOS No. 2,311,638. The compounds of the formula V are generally available, or can likewise be prepared by a conventional process.

The Examples which follow illustrate the preparation of the compounds of the formula I by the above process. Parts by weight bear the same relation to parts by volume as that of the kilogram to the liter.

EXAMPLE 1

A suspension of 4.2 parts by weight of sodium disulfide in 50 parts by volume of ethanol was added, at room temperature, to a solution of 35.2 parts by weight of 3-(2'-chloro-4'-trifluoromethylphenoxy)-6-nitrochlorobenzene in 100 parts by volume of ethanol, the reaction mixture was stirred for a further 40 hours, and the precipitate was then filtered off under suction, stirred with water and again filtered off under suction. 31 parts by weight (89% yield) of bis-[3-(2'-chloro-4'-trifluoromethylphenoxy)-6-nitrophenyl]disulfide of melting point 161°–165° C. were obtained (compound No. 1).

EXAMPLE 2

A suspension of 34.9 parts by weight of 3-(2'-chloro-4'-trifluoromethylphenoxy)-6-nitrophenyl disulfide in 200 parts by volume of absolute methylene chloride was saturated, at room temperature, with chlorine, and stirring was continued for a further 12 hours. The reaction solution was filtered, the filtrate was evaporated down under reduced pressure and the oily residue was crystallized by trituration. 37 parts by weight (96% yield) of 3-(2'-chloro-4'-trifluoromethylphenoxy)-6-nitrobenzenesulfenyl chloride of melting point 74°–78° C. were obtained (compound No. 2).

EXAMPLE 3

5.3 parts by weight of methyl thioglycolate were added dropwise to a solution of 19.2 parts by weight of 3-(2'-chloro-4'-trifluoromethylphenoxy)-6-nitrobenzenesulfenyl chloride in 100 parts by volume of absolute ether at room temperature, the reaction mixture was stirred for a further two hours and then evaporated to dryness under reduced pressure, and the oily residue was crystallized using diisopropyl ether. 25 parts by weight (90% yield) of 3-(2'-chloro-4'-trifluoromethylphenoxy)-6-nitrophenyl methoxycarbonylmethyl disulfide of melting point 66°–68° C. were obtained (compound No. 3).

EXAMPLE 4

1.62 parts by weight of ethanethiol and 2.6 parts by weight of triethylamine were added simultaneously to a solution of 10 parts by weight of 3-(2'-chloro-4'-trifluoromethylphenoxy)-6-nitrobenzenesulfenyl chloride in 100 parts by volume of absolute ether, and stirring was continued for a further 2 hours at room temperature. The reaction mixture was filtered, and the filtrate was extracted with dilute aqueous hydrochloric acid and water, dried over magnesium sulfate, filtered, and evaporated down under reduced pressure. 8 parts by weight (98% yield) of 3-(2'-chloro-4'-trifluoromethylphenoxy)-6-nitrophenyl ethyl disulfide of refractive index $n_D^{25}$: 1.6067 were obtained (compound No. 4).

EXAMPLE 5

3.1 g of methylamine in the form of a 40% strength aqueous solution were added to a solution of 19.2 parts by weight of 3-(2'-chloro-4'-trifluoromethylphenoxy)-6-nitrobenzenesulfenyl chloride in 100 parts by volume of ether, and stirring was continued for a further 2 hours at room temperature. The organic phase was separated off, dried with magnesium sulfate, filtered, and evaporated down under reduced pressure. 17.5 parts by weight (95% yield) of 3-(2'-chloro-4'-trifluoromethylphenoxy)-6-nitrobenzene-N-methylsulfenamide of refractive index $n_D^{25}$: 1.6109 were obtained (compound No. 5).

A similar procedure can be used to obtain, for example, the following compounds of the formula

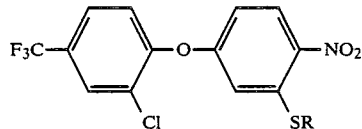

| Ex. no. | R HS— | M.p. [°C.]; $n_D^{25}$ | Wavelength of the band in the infrared spectrum |
|---|---|---|---|
| 6 | HS— | | |
| 7 | methylthio | | |
| 8 | n-propylthio | | |

-continued

| Ex. no. | R | M.p. [°C]; $n_D^{25}$ | Wavelength of the band in the infrared spectrum |
|---|---|---|---|
| 9 | n-butylthio | | 1.5981 |
| 10 | isopropylthio | | |
| 11 | s-butylthio | 55–59 | |
| 12 | 2-methyl-butylthio | 44–48 | |
| 13 | tert.-butylthio | 80–85 | |
| 14 | dodecylthio | | 1.5601 |
| 15 | methoxymethylthio | | |
| 16 | methoxyethylthio | | |
| 17 | methylthiomethylthio | | |
| 18 | methylthioethylthio | | |
| 19 | dodecylthioethylthio | | 1.5679 |
| 20 | dimethylaminoethylthio | | |
| 21 | chloroethylthio | | |
| 22 | fluoroethylthio | | |
| 23 | benzylthio | | |
| 24 | 4-chlorobenzylthio | 89–94 | |
| 25 | phenethylthio | 68–72 | |
| 26 | ethenylthio | | |
| 27 | ethinylthio | | |
| 28 | —S—CH$_2$COOH | | |
| 29 | —S—CH(CH$_3$)—COOH | | |
| 30 | —S—CH$_2$COOC$_3$H$_7$(n) | | |
| 31 | —S—CH$_2$COOC$_2$H$_5$ | 80–83 | |
| 32 | —S—CH(CH$_3$)COOCH$_3$ | | |
| 33 | —S—CH(CH$_3$)COOC$_2$H$_5$ | | |
| 34 | —S—CH$_2$CH$_2$COOC$_{12}$H$_{25}$ | | |
| 35 | —S—CH$_2$COOC$_{18}$H$_{37}$ | | |
| 36 | —S—CH$_2$CONHCH$_3$ | | |
| 37 | —S—CH(CH$_3$)CONHCH$_3$ | | |
| 38 | cyclopentylthio | | |
| 39 | cyclohexylthio | 81–86 | |
| 40 | phenylthio | | |
| 41 | 4-chlorophenylthio | 81–84 | |
| 42 | 4-methoxyphenylthio | | 1.6315 |
| 43 | 3-chlorophenylthio | 81–85 | |
| 44 | 2,4-dichlorophenylthio | | |
| 45 | 2,6-dichlorophenylthio | | |
| 46 | 3-trifluoromethylphenylthio | 83–87 | |
| 47 | 4-methylphenylthio | | |
| 48 | 2,4,5-trichlorophenylthio | | |
| 49 | 2,5-dichlorophenylthio | | |
| 50 | pentachlorophenylthio | | |
| 51 | 2-methylphenylthio | | |
| 52 | 2,3,4-trichlorophenylthio | | |
| 53 | 4-fluorophenylthio | | |
| 54 | hydroxy | | |
| 55 | methoxy | 59–62 | |
| 56 | ethoxy | 64–68 | |
| 57 | n-propoxy | 54–56 | |
| 58 | i-propoxy | 65–68 | |
| 59 | n-heptoxy | | 1.5669 |
| 60 | t-butoxy | 98–102 | |
| 61 | 2-methoxyethoxy | 79–82 | |
| 62 | 2-ethoxy-ethoxy | | |
| 63 | 2-ethylthio-ethoxy | | |
| 64 | 2-methylthio-ethoxy | | |
| 65 | 2-chloroethoxy | 78–81 | |
| 66 | 2-fluoroethoxy | | |
| 67 | benzyloxy | 101–104 | |
| 68 | 4-chlorobenzyloxy | 109–112 | |
| 69 | 2-phenylethoxy | 72–75 | |
| 70 | allyloxy | | |
| 71 | propargyloxy | | |
| 72 | —O—CH$_2$COOH | | |
| 73 | —O—CH—COOH<br>   \|<br>   CH$_3$ | | |
| 74 | —O—CH$_2$COOCH$_3$ | | |
| 75 | —O—CH$_2$COOC$_2$H$_5$ | | |
| 76 | —O—CHCOOCH$_3$<br>   \|<br>   CH$_3$ | | |
| 77 | —O—CHCOOC$_2$H$_5$<br>   \|<br>   CH$_3$ | 70–74 | |
| 78 | —O—CH$_2$COOC$_{12}$H$_{25}$ | | |
| 79 | —O—CH$_2$CONHCH$_3$ | | |
| 80 | —O—CHCONHCH$_3$<br>   \|<br>   CH$_3$ | | |
| 81 | cyclopentoxy | 83–87 | |
| 82 | cyclohexoxy | 79–83 | |
| 83 | phenoxy | | |
| 84 | 4-chlorophenoxy | | 1.6148 |
| 85 | 3-chlorophenoxy | | |
| 86 | 4-fluorophenoxy | | |
| 87 | 2,4-dichlorophenoxy | | 1.6194 |
| 88 | 4-methoxyphenoxy | | |
| 89 | 3-trifluoromethylphenoxy | 77–80 | |
| 90 | 4-methylphenoxy | | |
| 91 | 2,6-dichlorophenoxy | | |
| 92 | 2,4-dibromophenoxy | | |
| 93 | 3-bromophenoxy | | |
| 94 | 3-fluorophenoxy | | |
| 95 | 3,5-dimethylphenoxy | | 1.6141 |
| 96 | ethylamino | | |
| 97 | n-propylamino | | |
| 98 | isopropylamino | | 1.5871 |
| 99 | n-butylamino | | 1.5832 |
| 100 | isobutylamino | 58–63 | |
| 101 | t-butylamino | 101–104 | |
| 102 | n-hexylamino | | 1.5736 |
| 103 | n-dodecylamino | | 1.5494 |
| 104 | 2-ethyl-butyl-amino | | 1.5736 |
| 105 | pent-2-ylamino | | |
| 106 | 1,1-dimethyl-butyl-amino | 66–69 | |
| 107 | pent-3-yl-amino | | |
| 108 | heptadecylamino | | |
| 109 | n-heptylamino | | 1.5772 |
| 110 | 2,2-dimethylpropylamino | 98–102 | |
| 111 | tetradecylamino | 109–112 | |
| 112 | (5-methyl)-2-octyl-amino | | |
| 113 | (2,4-dimethyl)-3-pentyl-amino | | |
| 114 | (5-methyl)-3-heptyl-amino | | |
| 115 | (2,6-dimethyl)-4-heptyl-amino | | |
| 116 | tert.-octyl-amino | | |
| 117 | cetylamino | 45–48 | |
| 118 | 2-hydroxyethylamino | | 1.5965 |
| 119 | 2-methoxyethylamino | | 3380 cm$^{-1}$ (NH) |
| 120 | 3-methoxypropylamino | | |
| 121 | 3-isopropoxy-propylamino | | |
| 122 | di-methoxyethyl-amino | | 1.5711 |
| 123 | 3-n-hexyloxypropylamino | | |
| 124 | 3-lauryloxypropylamino | | |
| 125 | ethoxy-sec.butyl-amino | | |
| 126 | 2-benzylthioethylamino | | |
| 127 | 2-octylthioethylamino | | |
| 128 | 4-ethylthio-tert.butylamino | | |
| 129 | methylthioisopropylamino | | |
| 130 | methylthiopropylamino | | |
| 131 | methylthioethylamino | | 1.6087 |
| 132 | methylaminoethylamino | | |
| 133 | ethylaminoethylamino | | |
| 134 | dimethylaminoethylamino | | |
| 135 | diethylaminoethylamino | | |
| 136 | chloroethylamino | | |
| 137 | fluoroethylamino | | |

| Ex. no. | R | M.p. [°C.]; $n_D^{25}$; | Wavelength of the band in the infrared spectrum |
|---|---|---|---|
| 138 | benzylamino | | |
| 139 | phenethylamino | | 1.6121 |
| 140 | allylamino | | |
| 141 | propargylamino | | |
| 142 | —NH—CH$_2$—COOH | | |
| 143 | —NH—CH(CH$_3$)COOH | | |
| 144 | —NH—CH$_2$COOCH$_3$ | | |
| 145 | —NH—CH(CH$_3$)COOCH$_3$ | | |
| 146 | —NH—CH$_2$COOC$_2$H$_5$ | | |
| 147 | —NH—CH(CH$_3$)COOC$_2$H$_5$ | | |
| 148 | —NH—CH$_2$CONHCH$_3$ | | |
| 149 | cyclopropylamino | | |
| 150 | cyclobutylamino | | |
| 151 | cyclopentylamino | | |
| 152 | cyclohexylamino | | |
| 153 | phenylamino | 105–110 | |
| 154 | 4-chlorophenyl-amino | 95–98 | |
| 155 | 3-trifluoromethylphenylamino | 90–95 | |
| 156 | 4-fluorphenylamino | | |
| 157 | 4-methylphenylamino | | |
| 158 | 4-cyanphenylamino | | |
| 159 | 4-nitrophenylamino | | |
| 160 | 3,4-dichlorophenylamino | 55–60 | |
| 161 | 4-methoxyphenylamino | | |
| 162 | 3,5-ditrifluormethylphenylamino | | |
| 163 | 3-methyl-4-fluorophenylamino | | |
| 164 | 2,6-difluorophenylamino | | |
| 165 | 3,4,5-trifluorophenylamino | | |
| 166 | 3-trifluoromethoxyphenylamino | | |
| 167 | 3-tetrafluoroethoxyphenylamino | | |
| 168 | —NH—OH | | |
| 169 | methoxyamino | | |
| 170 | ethoxyamino | | |
| 171 | benzyloxyamino | | |
| 172 | phenoxyamino | | |
| 173 | 4-chlorophenoxyamino | | |
| 174 | 4-methylphenoxyamino | | |
| 175 | —N(CH$_3$)(OCH$_3$) | 58–61 | |
| 176 | —N(CH$_3$)(OC$_2$H$_5$) | | |
| 177 | —N(OCH$_3$)(cyclohexyl) | | |
| 178 | —NH—NH$_2$ | | |
| 179 | —NH—NH(CH$_3$) | | |
| 180 | —NH—N(CH$_3$)$_2$ | | |
| 181 | —NH—NH(C$_6$H$_5$) | | |
| 182 | —NH—NH(4-chlorophenyl) | | |
| 183 | —N(CH$_3$)—NH(C$_6$H$_5$) | | |
| 184 | —N(CH$_3$)—N(CH$_3$)C$_6$H$_5$ | | |
| 185 | morpholino | 126–130 | |
| 186 | 2,6-dimethylmorpholino | | |
| 187 | piperazino | | |
| 188 | 2,6-dimethylpiperazino | | |
| 189 | N—methyl-piperazino | | |
| 190 | amino | 82–86 | |
| 191 | dimethylamino | | 1.6022 |
| 192 | 2-methyl-n-butylamino | 47–49 | |
| 193 | 1-ethyl-n-propylamino | 70–73 | |
| 194 | O—CH$_2$CO—n-C$_4$H$_9$ (C=O) | | 1.5504 |
| 195 | O—C(CH$_3$)$_2$CO—n-C$_3$H$_7$ (C=O) | | 1.5181 |
| 196 | O—CH$_2$C(CH$_3$)$_2$COCH$_3$ (C=O) | | 1.5710 |
| 197 | O—CH$_2$C(=O)—N(cyclooctyl ring) | | 1.5653 |
| 198 | O—C$_6$H$_4$—OCH(CH$_3$)CO—n-C$_4$H$_9$ | | 1.5430 |

The following diphenyl ethers of the formula I, for instance, may also be obtained:

| Ex. no. | Z$^2$ | R | M.p. [°C.]; $n_D^{25}$; Wavelength of a band in the infrared spectrum |
|---|---|---|---|
| 199 | 2,4-dichlorphenoxy | ethylthio | |
| 200 | " | methylamino | |
| 201 | " | phenylamino | |
| 202 | 2,4-dibromphenoxy | ethylthio | |
| 203 | " | methylamino | |
| 204 | 3-chloro-4-trifluoromethylphenoxy | ethylthio | |
| 205 | 3-chloro-4-trifluoromethylphenoxy | methylamino | |
| 206 | 2,6-dichloro-4-trifluoromethylphenoxy | ethylthio | |
| 207 | 2,6-dichloro-4-trifluoromethylphenoxy | —S—CH$_2$COOCH$_3$ | |
| 208 | 2,6-dichloro-4-trifluoromethylphenoxy | —S—CH(CH$_3$)COOCH$_3$ | |
| 209 | 2,6-dichloro-4-trifluoromethylphenoxy | methylamino | |
| 210 | 2,6-dichloro-4-trifluoromethylphenoxy | benzylamino | |
| 211 | 2,6-dichloro-4-trifluoromethylphenoxy | methoxyamino | |
| 212 | 2,6-dichloro-4-trifluoromethylphenoxy | benzyloxyamino | |
| 213 | 2,6-dichloro-4-trifluoromethylphenoxy | —N(CH$_3$)(OCH$_3$) | |

The diphenyl ethers of the formula I, or herbicidal agents containing them, may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90%, by weight of active ingredient.

Eamples of formulations are as follows:

I. 90 parts by weight of compound no. 3 is mixed with 10 parts by weight of N-methyl-alpha-pyrrolidone. A mixture is obtained which is suitable for application in the form of very fine drops.

II. 10 parts by weight of compound no. 4 is dissoled in a mixture consisting of 90 parts by weight of xylene, 6 parts by weight of the adduct of 8 to 10 moles of ethylene oxide and 1 mole of oleic acid-N-monoethanolamide, 2 parts by weight of the calcium salt of dodecylbenzenesulfonic acid, and 2 parts by weight of the adduct of 40 moles of ethylene oxide and 1 mole of castor oil.

III. 20 parts by weight of compound no. 31 is dissolved in a mixture consisting of 60 parts by weight of cyclohexanone, 30 parts by weight of isobutanol, 5 parts by weight of the adduct of 7 moles of ethylene oxide and 1 mole of isooctylphenol, and 5 parts by weight of the adduct of 40 moles of ethylene oxide and 1 mole of castor oil.

IV. 20 parts by weight of compound no. 2 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 80 parts by weight of compound no. 41 is well mixed with 3 parts by weight of the sodium salt of diisobutylnaphthalene-alpha-sulfonic acid, 10 parts by weight of the sodium salt of a lignin-sulfonic acid obtained from a sulfite waste liquor, and 7 parts by weight of powdered silica gel, and triturated in a hammer mill.

VI. 5 parts by weight of compound no. 55 is intimately mixed with 95 parts by weight of particulate kaolin. A dust is obtained containing 5% by weight of the active ingredient.

VII. 30 parts by weight of compound no. 56 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts of compound no. 131 is intimately mixed with 2 parts of the calcium salt of dodecylbenzenesulfonic acid, 8 parts of a fatty alcohol polyglycol ether, 2 parts of the sodium salt of phenolsulfonic acid-urea-formaldehyde condensate and 68 parts of a paraffinic mineral oil. A stable oily dispersion is obtained.

Application may be effected pre- or postemergence. Preferably, the novel active ingredients, or agents containing them, are applied after emergence of the unwanted plants. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The amount of active ingredient applied depends on the time of the year, the objective to be achieved and the growth stage of the plants, and varies from 0.005 to 4 kg/ha, and preferably from 0.03 to 3.0 kg/ha.

The action of diphenyl ethers of the formula I on the growth of unwanted and crop plants is demonstrated in greenhouse experiments.

The vessels employed were plastic flowerpots having a volume of 300 cm$^3$, and which were filled with a sandy loam containing about 1.5% humus. The seeds of the test plants were sown shallow, and separately, according to species. For the preemergence treatment, the active ingredients were applied to the surface of the soil immediately after the seeds had been sown. The compounds were emulsified or suspended in water as vehicle, and sprayed through finely distributing nozzles. The application rate was 3.0 kg of active ingredient per hectare. After the agents had been applied, the vessels were lightly sprinkler-irrigated to induce germination and growth and to activate the chemical agents. Transparent plastic covers were then placed on the vessels until the plants had taken root. The cover ensured uniform germination of the plants, insofar as this was not impaired by the chemicals.

For the postemergence treatment, the plants were first grown in the vessels to a height of from 3 to 15 cm, depending on growth form, before being treated. The rice and soybean plants used for this treatment method were grown in a peat-enriched substrate. No impairment of the results need be feared, as the plants were treated postemergence. For this treatment, either plants which had been sown directly in the pots and grown there were selected, or plants which had been grown separately as seedlings and transplanted to the experiment vessels a few days before treatment. The application rates for postemergence treatment varied from ingredient to ingredient, and were from 0.03 to 0.25 kg/ha.

The pots were set up in the greenhouse-species from warmer areas at from 20° to 35° C., and species from moderate climates at 10° to 25° C. The experiments were run for from 2 to 4 weeks. During this period, the plants were tended and their reactions to the various treatments assessed. The scale used for assessment was 0 to 100, 0 denoting no damage or normal emergence, and 100 denoting nonemergence or complete destruction of at least the visible plant parts.

The plants used in the greenhouse experiments were *Amaranthus retroflexus, Arachys hypogaea, Chenopodium album, Euphorbia geniculata, Glycine max., Impomoea* spp., Lamium spp., *Oryza sativa, Sida spinosa, Sinapis alba, Solanum nigrum, Triticum aestivum* and *Viola tricolor.*

On investigations into selective herbicidal properties, active ingredients nos. 2, 3, 4, 5 and 31 combated broadleaved weeds while selectively sparing crop plants. In these investigations, compounds nos. 41, 42, 43, 98 and 131 also had a very good herbicidal action, and the crop plants, such as groundnuts and rice, were (if damaged at all) only damaged slightly and temporarily. Compounds nos. 55 and 77 at 0.06 kg/ha, and nos. 82, 87 and 106 at 0.25 kg/ha had a good action on broadleaved weeds without—or only temporary and slight—damage to wheat. Further, for example compound no. 56, at 0.006 kg/ha, combated unwanted broadleaved plants very well and was selective in various crops.

For example compounds nos. 56, 194, 197 and 198, at 3.0 kg/ha, had a herbicidal action on preemergence application.

In view of the many application methods possible, the compounds according to the invention may be used in a large number of crop plants for removing unwanted plant growth, preferably broadleaved annual species. The following crop plants may be mentioned by way of example:

| Botanical name | Common name |
| --- | --- |
| Allium cepa | onions |
| Ananas comosus | pineapples |
| Arachis hypogaea | peanuts (groundnuts) |
| Asparagus officinalis | asparagus |
| Avena sativa | oats |
| Beta vulgaris spp. altissima | sugarbeets |
| Beta vulgaris spp. rapa | fodder beets |
| Beta vulgaris spp. esculenta | table beets, red beets |
| Brassica napus var. napobrassica | |
| Camellia sinensis | tea plants |
| Carthamus tinctorius | safflower |
| Carya illinoinensis | pecan trees |
| Citrus limon | lemons |
| Citrus maxima | grapefruits |
| Citrus reticulata | mandarins |
| Citrus sinensis | orange trees |
| Coffea arabica (Coffea canephora, Coffea liberica) | coffee plants |
| Cucumis melo | melons |
| Cynodon dactylon | Bermudagrass in turf and lawns |
| Elais guineensis | oil palms |
| Fragaria vesca | strawberries |
| Glycine max | soybeans |
| Gossypium hirsutum (Gossypium arboreum Gossypium herbaceum Gossypium vitifolium) | cotton |
| Helianthus annuus | sunflowers |
| Helianthus tuberosus | |
| Hevea brasiliensis | rubber plants |
| Hordeum vulgare | barley |
| Humulus lupulus | hops |
| Ipomoea batatas | sweet potatoes |
| Juglans regia | walnut trees |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Mentha piperita | peppermint |
| Musa spp. | banana plants |
| Nicothiana tabacum (N. rustica) | tobacco |
| Olea europaea | olive trees |
| Oryza sativa | rice |
| Panicum miliaceum | |
| Phaseolus lunatus | limabeans |
| Phaseolus mungo | mungbeans |
| Phaseolus vulgaris | snapbeans, green beans, dry beans |
| Pennisetum glaucum | |
| Petroselinum crispum spp. tuberosum | parsley |
| Picea abies | Norway spruce |
| Abies alba | fir trees |
| Pinus spp. | pine trees |
| Pisum sativum | English peas |
| Prunus avium | cherry trees |
| Prunus domestica | plum trees |
| Prunus dulcis | almond trees |
| Prunus persica | peach trees |
| Pyrus communis | pear trees |
| Ribes sylvestre | redcurrants |
| Ribes uva-crispa | gooseberries |
| Ricinus Communis | castor-oil plants |
| Saccharum officinarum | sugar cane |
| Secale cereale | rye |
| Solanum tuberosum | Irish potatoes |
| Sorghum bicolor (s. vulgare) | sorghum |
| Sorghum dochna | |
| Theobroma cacao | cacao plants |
| Trifolium pratense | red clover |
| Triticum aestivum | wheat |
| Vaccinium corymbosum | blueberries |
| Vaccinium vitis-idaea | cranberries |
| Vicia faba | tick beans |
| Vigna sinensis (V. unguiculata) | cow peas |
| Vitis vinifera | grapes |
| Zea mays | Indian corn, sweet corn, maize |

To increase the spectrum of action and to achieve synergistic effects, the novel compounds according to the invention may be mixed and applied together with numerous representatives of other herbicidal or growth-regulating active ingredient groups. Examples of suitable mixture components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, cyclohexane-1,3-dione derivatives, etc.

It may also be useful to apply the novel compounds, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. Non-phytotoxic oils and oil concentrates may also be added.

We claim:

1. A diphenyl ether of the formula

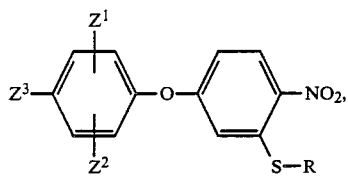

where $Z^1$ and $Z^2$ independently of one another are each hydrogen, halogen, nitro, cyano, carboxyl, $C_1$–$C_4$-alkyl, $C_1$–$C_4$-haloalkyl or $C_1$–$C_4$-alkoxy, $Z^3$ is halogen, nitro, cyano, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylmercapto, $C_1$–$C_4$-haloalkylmercapto, $C_1$–$C_4$-alkylsulfinyl, $C_1$–$C_4$-haloalkylsulfinyl, $C_1$–$C_4$-alkylsulfonyl or $C_1$–$C_4$-haloalkylsulfonyl, and R is, halogen or —X—$R^1$, where X is oxygen or sulfur and $R^1$ is hydrogen, $C_1$–$C_{20}$-alkyl, $C_2$–$C_{20}$-alkoxyalkyl, $C_2$–$C_{20}$-alkylthioalkyl, $C_2$–$C_{20}$-alkylaminoalkyl, $C_3$–$C_{20}$-dialkylaminoalkyl, $C_1$–$C_{20}$-haloalkyl, an unsubstituted or halogen-substituted phenyl alkyl radical of 7 to 9 carbon atoms, $C_2$–$C_8$-alkenyl, $C_2$–$C_8$-haloalkenyl or $C_2$–$C_8$-alkynyl, carboxyalkyl, alkoxycarbonylalkyl or carbamylalkyl of not more than 6 carbon atoms, cycloalkyl of 3 to 20 carbon atoms or unsubstituted phenyl or phenyl substituted by halogen, $C_1$–$C_4$-alkyl, $C_1$–$C_4$-haloalkyl, cyano or —O—(CHR$^4$)$_n$—COOR$^5$, where $R^4$ is hydrogen, methyl, ethyl or propyl, $R^5$ is alkyl of 1 to 4 carbon atoms and n is 1, 2, or 3, R is —NR$^2$R$^3$, where $R^2$ and $R^3$ are identical or different and have the meanings stated for $R^1$, or if $R^3$ is hydrogen or $C_1$–$C_4$-alkyl, $R^2$ is hydroxyl or $C_1$–$C_{20}$-alkoxy, or is $C_1$–$C_{20}$-alkoxy which is substituted by $C_1$–$C_6$-alkoxy, $C_1$–$C_6$-alkylthio, $C_1$–$C_6$-alkylamino, $C_2$–$C_6$-dialkylamino, halogen, carboxylalkyl, alkoxycarbonyl or phenyl, or is unsubstituted phenoxy or phenoxy substituted by halogen or $C_1$–$C_4$-alkyl or unsubstituted, $C_1$–$C_{20}$-alkyl-substituted or phenyl-substituted amino, or $R^2$ and $R^3$ together with the nitrogen atom to which they are attached are azetidino, pyrrolidino, piperidino, morpholino, 2,6-dimethylmorpholino, piperazino, 2,6-dimethylpiperazino, N-methylpiperazino or N-ethylpiperazino .

2. A diphenyl ether of the formula I as claimed in claim 1, where $Z^1$, $Z^2$ and $Z^3$ are in the 2-, 4-, and 6-positions and $Z^1$ and $Z^2$ independently of one another are each halogen or $C_1$–$C_4$-haloalkyl and $Z^3$ is halogen, $C_1$–$C_4$ haloalkyl or $C_1$–$C_4$-haloalkylmercapto, and R is halogen or —X—$R^1$, where X is oxygen or sulfur and $R^1$ is $C_1$–$C_8$-alkyl, $C_2$–$C_6$-alkoxyalkyl, $C_2$–$C_6$-carboxyalkyl or $C_3$–$C_6$-alkoxycarbonylalkyl, or R is —NR$^2$R$^3$, where $R^2$ and $R^3$ are identical or different and are each hydrogen, $C_1$–$C_{10}$-alkyl, $C_2$–$C_6$-alkoxyalkyl, $C_2$–$C_6$-alkylthioalkyl or unsubstituted or halogen-substituted phenyl, or where $R^3$ is hydrogen or $C_1$–$C_4$-alkyl and $R^2$ is $C_1$–$C_4$-alkoxy or unsubstituted or $C_1$–$C_8$-alkyl-substituted amino.

3. A diphenyl ether of the formula I as claimed in claim 1, where $Z^1$ is hydrogen, $Z^2$ and $Z^3$ are halogen or $C_1$–$C_4$-haloalkyl and R is —X—$R^1$, X denoting oxygen and $R^1$ being $C_1$–$C_4$-alkyl.

4. 3-(2'-Chloro-4'-trifluoromethylphenoxy)-6-nitrobenzene-N-methylsulfenamide.

5. Methyl 3-(2'-chloro-4'-trifluoromethylphenoxy)-6-nitrobenzenesulfenate.

6. Ethyl 3-(2'-chloro-4'-trifluoromethylphenoxy)-6-nitrobenzenesulfenate.

7. A herbicide containing inert additives and an effective amount of a diphenyl ether of the formula I as claimed in claim 1.

8. A herbicide containing inert additives and an effective amount of a diphenyl ether as claimed in claim 2.

9. A herbicide containing inert additives and an effective amount of a diphenyl ether as claimed in claim 3.

10. A process for combating the growth of unwanted plants, wherein the unwanted plants or the area to be kept free from unwanted plant growth are treated with a herbicidally effective amount of a diphenyl ether of the formula I as claimed in claim 1.

* * * * *